United States Patent [19]
Sawyer et al.

[11] 4,390,630
[45] Jun. 28, 1983

[54] HEMENTIN--A FIBRINOLYTIC AGENT

[75] Inventors: Roy T. Sawyer, Penclawdd, Wales; Gunther S. Stent, Kensington, Calif.; Andrei Z. Budzynski, Glenside; Stephanie A. Olexa, Hellertown, both of Pa.

[73] Assignee: The Regents of the University of California, Berkeley, Calif.

[21] Appl. No.: 201,655

[22] Filed: Oct. 28, 1980

[51] Int. Cl.$^3$ .................. C12N 9/64; C12N 9/48; C12N 9/50; A61K 37/54
[52] U.S. Cl. .................. 435/226; 435/814; 435/816; 435/212; 435/219; 424/94
[58] Field of Search ............. 435/212, 217, 219, 226, 435/814, 816; 424/94

[56] References Cited
PUBLICATIONS

Hamou Da, "Demonstration of an Enzyme Contributing to the Inhibition of the Coagulation of Blood Ingested by Hematokhageous Insect *Rhodnius Prolixus*.-"*Arch. Inst. Pasteur Tunus* 55:(1978) pp. 70–88.

Kelen et al., "Fibrmolytic Substance (Hementerin) of Brazillian Blood-Sucking Leeches, (*Haementeria Lutzi*) *Haemostasis*, 4(1) (1975) pp. 51–64.

Bagdy et al., "Hirudin" *Methods in Enzymology* vol. 45, (1976) pp. 669–678.

Otroshko et al., "A Study of *Aspergillus Ochraceus* Proteolytic System and its Plasmocoagulating and Fibrimolytic Activities" *Mikrobiologiya* 48(4) (1979) pp. 645–652.

Imshenetskii et al., "Application of the Tissue Culture Method for Assaying the Toxicity of Fibrimolytic Preparations" *IEV. Akad. Nauk. SSSR Ser. Biol.*, 4 (1977) pp. 602–605.

von Kaulla, "In Vitro Dissolution of Human Clots by Whisky", *Lancet* 2 (1941) (Nov. 8, 1975) p. 917.

*Primary Examiner*—Thomas G. Wiseman
*Assistant Examiner*—John E. Tarcza
*Attorney, Agent, or Firm*—Bertram I. Rowland

[57] ABSTRACT

Novel fibrinolytic factors obtained from the salivary glands of *Haementeria ghilianii*. Proteins having molecular weights under about 100,000 are isolated from the salivary glands of *H. ghilianii*. The proteins show cathodic mobility in electrophoresis and uninhibited peptidase activity with fibrinogen in plasma.

5 Claims, No Drawings

HEMENTIN--A FIBRINOLYTIC AGENT

The invention described herein was made in the course of, or under, a grant from the National Institutes of Health.

BACKGROUND OF THE INVENTION

1. Field of the Invention

Blood clotting is a complex chemical process involving a number of constituents. Blood sucking animals have the capability of inhibiting the host's blood from coagulating. There are basically two types of anticoagulant substances: Inhibitors of the clotting catalyst, e.g. inhibitors of thrombin; and fibrinolytic proteases.

The best-understood of these anticoagulants is hirudin, secreted by the leech *Hirudo medicinalis*. Hirudin is an anticoagulant of the first category, binding irreversibly and with high affinity to human thrombin. Another anticoagulant, of the second category, was obtained from the leech *Haementeria lutzi* Pinto 1920, which lacks any direct proteolytic activity but activates the host plasminogen.

Depending upon the nature and effectiveness of blood anticoagulants, blood anticoagulants can find a wide variety of applications. Therefore, there has been a continuing interest in obtaining blood anticoagulants which demonstrate different types of anticoagulant activity.

2. Description of the Prior Art

Hirudin has been characterized by Bagdy et al., Methods Enzymol. 45, 669-678, 1976 and Markwardt, Zeitschrift Physiol, Chem. 308: 147-157, 1957. The anticoagulant hementerin from *Haementeria lutzi* Pinto 1920 is described in an article by Kellen and Rosenfeld, Haemostasis 4: 51-64, 1975.

SUMMARY OF THE INVENTION

A fibrinolytic protease from *Haementeria ghilianii* is obtained from salivary gland cells. The fibrinolytic factor in the salivary glands is active in plasma in degrading fibrinogen and fibrin. As distinct from other anticoagulants from blood sucking animals, the anticoagulating factor of *Haementeria ghilianii* acts as an uninhibited protease in degrading the fibrinogen, rather than activating the host fibrinolytic system or inhibiting the coagulating system.

DESCRIPTION OF THE SPECIFIC EMBODIMENTS

A novel anticoagulant factor, hementin, is provided which is isolated from the salivary glands of *Haementeria ghilianii*. The factor is found in the cytosol and can be concentrated by ultracentrifugation, so as to be free of particulate matter and cell debris.

In electrophoresis, both polyacrylamide gel and cellulose acetate, hementin shows cathodic mobility.

The hementin is obtained from the anterior and posterior salivary glands of *H. ghilianii*. The predominant protein observed in electrophoresis in the anterior gland extract has a molecular weight of about 37 kdal, while the posterior gland has two major components with molecular weights believed to be about 80 kdal and 13.5 kdal. The primary activity is found with the component referred to as the 80 kdal component. The proteins have disulfide linkages, which are reducible.

The enzymatic properties are shown to be different from plasmin by a comparison of the fibrinogen degradation products generated by digestion with either the anterior or posterior gland extract, whether the digest is reduced or unreduced. As compared to the well characterized plasmin degradation products, with hementin seven fibrinogen derivatives are formed with molecular weights in the range of 30-300 kdal. The Aα polypeptide chain of fibrinogen appears to be cleaved first by salivary proteolysis, followed by cleavage of the γ and B↑ chains. This fibrinogen degradation pattern is found to be the same even in the presence of human plasminogen or calcium chloride (5 mM), although digestion proceeds slightly more slowly in the presence of the calcium ions.

The hementin is obtained by placing posterior glands in a buffer, homogenizing manually and then centrifuging. After washing the pellets, the mixture is centrifuged and the supernatants combined. Further purification can be achieved with preparative ultracentrifugation, or electrophoresis, with polyacrylamide gel in the presence of SDS (sodium dodecylsulfate) or cellulose acetate at a moderately basic pH. The active fractions of the salivary extract can be detected by determining lytic activity.

The following examples are offered by way of illustration and not by way of limitation.

Specimens of *Haementeria ghilianii* which have been collected from a French Guyana swamp and bred at the University of California, Berkeley, were employed. The salivary glands of *H. ghilianii* are stretched along the proboscis on either side and are encapsulated by a thin membrane. There are two bilateral pairs of glands: The anterior glands are large (20 mm long) and contain predominantly cells of large size (0.7 mm diameter); the posterior glands are small (5 mm long) and contain mostly cells of very small size (0.01 mm diameter). Anesthesized leeches were opened by a longitudinal incision on the dorsal midline, and the anterior and posterior salivary glands were removed separately without any surrounding tissue. The glands were freeze-dried and stored at −80° C. The leeches had not been allowed to feed for several months prior to dissection to increase the concentration of salivary enzymes.

To prepare a salivary extract, ten anterior or posterior glands were placed into 3 or 0.8 ml of 0.15 M Tris-HCl buffer, pH 7.8, respectively. The tissue was homogenized manually, and the homogenate subjected to centrifugation of 8,500 g for 10 min. and the supernatant decanted.

Preparative ultracentrifugation was carried out in a swinging-bucket rotor in a model L-50 centrifuge. Homogenates of salivary glands were fractionated according to the following scheme: 1,000×g for 20 min.; 12,000×g for 20 min. and 100,000×g for 60 min. The three pellets were suspended in 0.075 M sodium veronal buffer, pH 8.6. The resuspended pellets, the final supernatant, as well as the initial homogenate were tested on fibrin clots for lytic activity.

Results with fibrin clots showed that the fibrinolytic activity is found exclusively in the cytosol.

The total protein recovered from the posterior gland preparation was 72% as compared to 14% from the anterior gland preparation. However, total fibrinolytic activity is recovered in greater amount from the much larger anterior gland.

The anticoagulant activity of hementin was assessed by use of a thrombin clotting time test with either human or bovine plasma. A 0.05 M sodium veronal buffer containing 0.1 M sodium chloride, pH 7.75, was used. The substrates were diluted with the buffer, so that the fibrinogen concentration was 2.5 mg/ml. For testing, 0.1 ml of the substrate was mixed with 0.1 ml of the gland extract (0.6 mg/ml) (or buffer when the extract was omitted) and incubated at 37° for 5 min. either in the presence or absence of calcium chloride (5 mM). Then, 0.1 ml of human α-thrombin (10 units/ml) was added and the clotting time measured at 37° C. With both types of plasma, the clotting time was prolonged by the presence of extracts from the anterior salivary glands.

The observed effect is not due to the inactivation of thrombin by the extracts, since preincubation of human α-thrombin with the extracts at 37° C. for 10 min. does not result in any additional prolongation of the clotting time in the subsequent test.

In the next study, fibrinolytic activity was investigated. For this purpose, fibrin clots were formed by action of thrombin on human or bovine euglobulins. Under the conditions employed, such clots do not dissolve spontaneously. The test was performed employing a 0.05 M sodium phosphate buffer containing 0.1 M sodium chloride, pH 7.7. The substrates were diluted with the buffer to the final protein concentration of 2.5 mg/ml. For testing, 0.1 ml of the substrate was mixed with 0.1 ml of the gland extract (1 mg/ml) or buffer and 0.1 ml of human α-thrombin (10 units/ml) was added in the presence or absence of calcium chloride (5 mM). The clots were incubated at 37° C. and lysis time was measured. For positive control, plasmin (0.2 CTAu-nits/ml) was substituted for the gland extract. The following table indicates the results.

TABLE I

The Fibrinolytic Effect of the Anterior Salivary Gland Extract on Euglobulin Clots

| Substrate | Active Agent | CaCl$_2$ | Lysis Time (min) |
|---|---|---|---|
| Human Euglobulin Clot | Buffer | − | no lysis |
| | " | + | no lysis |
| | Extract | − | 15 |
| | " | + | 51 |
| | Plasmin | − | 52 |
| | " | + | 60 |
| Bovine Euglobulin Clot | Buffer | − | no lysis |
| | " | + | no lysis |
| | Extract | − | 6 |
| | " | + | 47 |
| | Plasmin | − | 240 |
| | " | + | 1000 |

The above data demonstrate the fibrinolytic activity of anterior salivary gland extracts. The data show that the clot lysis time due to salivary extracts is prolonged by the presence of 5 mM calcium ions and that it is longer for human euglobulin clots than for bovine euglobulin clots.

To test for the presence of an activator of human plasminogen in salivary extracts, fibrin clots were used on which the substrate was either enriched in or depleted of plasminogen. It was found that the extracts promoted the same rate of fibrinolysis on such special clots as on the normal clots. Therefore, it is concluded that neither the anterior nor posterior salivary gland contains a significant amount of plasminogen activator.

Tests were performed employing a mixture of extracts with human plasminogen, urokinase, streptokinase and α-thrombin, where each of these agents were preincubated with the salivary extract, and amidolysis measured. The amidolysis activity results indicated that the salivary glands do not contain a human plasminogen activator or any zymogen that is subject to activation by the above agents or by a component of the other gland.

Amidolytic activity was determined in a spectrophotometer at 405 nm employing a synthetic chromogenic substrate, H-D-Val-Leu-Lys-HN-C$_6$H$_4$NO$_2$. The results are described in the following Table II.

TABLE II

Amidolysis of Chromogenic Substrate by Leech Salivary Gland Extracts

| Active Agent | Rate μmoles/min/mg | Specific Activity CTAu/mg | Rate Equvalency μmoles/min/CTAu |
|---|---|---|---|
| Anterior gland | 15.4 | 0.044 | 350 |
| Posterior gland | 12.4 | 0.035 | 354 |
| Plasmin | 3645 | 12.7 | 287 |
| Trypsin | 8750 | 29.6 | 296 |

The specific activity is obtained from a plasmin calibration line. The ratio of the rate to the specific activity allows for the comparison of enzyme amidolytic activities.

To further characterize the hementin, the salivary gland extracts were subjected to electrophoresis. Polyacrylamide gel electrophoresis was performed in cylindrical tubes (0.5×9 cm) in 7% gels containing 0.1% SDS. (Weber and Osborn, J. Biol. Chem. 244: 4406–4412, 1969). Approximately 10 μg of protein was applied per gel and staining was by the method of Fairbanks et al., Biochemistry 10: 2606-2617, 1971. The conditions employed result in the dissociation of proteins into their polypeptide chains.

The resulting gels showed that the protein compositions of the anterior and posterior gland extracts were completely different, whether reduced or non-reduced extracts were examined. The predominant protein in the anterior gland extract had a molecular weight of 37 kdal and in the posterior gland, there were two major species, one about 80 kdal and the other 13.5 kdal.

The proteins present in the extracts were further characterized by electrophoresis on cellulose acetate conducted in a Microzone apparatus, Beckman, Palo Alto, California. A 0.075 M sodium veronal buffer, pH 8.6, was used. Approximately 5 μg of protein was applied per track and electrophoresed at 250 V and 6 mA for 20 min. The membrane was stained with 0.2% solution of Ponceau S and destained in 5% acetic acid. Dry stained membrane was made transparent in a methanol-:acetic acid (3:1) mixture and scanned in a densitometer.

As with the previous electrophoresis, the protein composition of anterior and posterior gland extracts was found to be completely different. The anterior gland extract contained a predominant protein with cathodic mobility. The posterior gland extract contained two major bands, one with cathodic and the other with anodic mobility. The fibrinolytic activity was located by incubating an unstained cellulose acetate electrophorogram overlayed with a fibrin clot. The zone with the fibrinolytic activity was found to have the same electrophoretic mobility in both gland extracts.

In accordance with the subject invention, a novel fibrinolytic protein composition is provided having as a major component, a compound believed to be of from about 80–85 kdal, which may exist as a single polypeptide or a protein of a plurality of units. This is important in that it indicates the insensitivity of hementin to the inhibitors of proteolytic enzymes present in plasma.

This makes hementin unique among known fibrinolytic enzymes and provides a highly desirable property as a thrombolytic agent for therapeutic dissolution of blood clots in patients. Hementin may also be available from other Haementeria e.g. *H. officinalis.*

Hementin can also fine use in inhibiting coagulation of whole blood, where whole blood is to be stored, in removal of blood stains, or other situations where clotting has occurred and it is desirable to dissolve the clot. The amount of the hementin employed will depend upon the purity of the composition, the rate at which the clot is to be dissolved, and the like.

The amount administered in a host to inhibit clotting will generally be in an amount sufficient to provide at least about 0.1 µg/ml and less than about 100 µg/ml, more usually less than about 50 µg/ml in the environment of the thrombus. The hementin will normally be administered in a physiologically acceptable vehicle, such as saline, buffered saline, or the like.

Although the foregoing invention has been described in some detail by way of illustration and example for purposes of clarity of understanding, it will be obvious that certain changes and modifications may be practiced within the scope of the appended claims.

What is claimed is:

1. Hementin, a polypeptide of between about 80 to about 85 kdal isolated from *Haementeria ghilianii*, characterized by having cathodic electrophoretic mobility on cellulose acetate in a 0.075 M sodium veronal buffer, pH 8.6; having anticoagulant activity which activity is independant of the inactivation of thrombin; and by having the ability to dissolve previously formed fibrin clots and having activity toward fibrinogen different from plasmin.

2. A fibronolytic proteinaceous composition comprising an extract from the salivary glands of *Haementeria ghilianii.*

3. A composition according to claim 2, wherein said salivary glands are anterior.

4. A composition according to claim 2, wherein said salivary glands are posterior.

5. A fibrinolytic proteinaceous composition having as a major component of a polypeptide of from about 80 to 85 kdal isolated from *Haementeria ghilianii*, said polypeptide characterized by having cathodic electrophoretic mobility on cellulose acetate in a 0.075 M sodium veronal buffer pH 8.6; by having anti-coagulant activity which activity is independant of the inactivation of thrombin; and by having the ability to dissolve previously formed fibrin clots and having activity toward fibrinogen different from plasmin.

* * * * *